United States Patent [19]

Bara et al.

[11] Patent Number: 5,637,291

[45] Date of Patent: Jun. 10, 1997

[54] SURFACTANT-FREE OIL-IN-WATER EMULSION STABILIZED BY HOLLOW THERMOPLASTIC PARTICLES

[75] Inventors: Isabelle Bara; Philippe Touzan, both of Paris, France

[73] Assignee: L'Oreal, Paris, France

[21] Appl. No.: 500,830

[22] Filed: Jul. 11, 1995

[30] Foreign Application Priority Data

Jul. 11, 1994 [FR] France ................................. 94 08561

[51] Int. Cl.$^6$ ....................................................... A61K 7/00
[52] U.S. Cl. ........................... 424/59; 424/63; 424/401; 424/70.11; 514/944; 514/938; 524/209; 524/801
[58] Field of Search .............................. 424/59, 63, 401, 424/70.11; 514/944, 938; 524/209, 801

[56] References Cited

U.S. PATENT DOCUMENTS

| 5,223,559 | 6/1993 | Arraudeau et al. ................. 524/47 |
| 5,246,780 | 9/1993 | Farer et al. ......................... 428/404 |

FOREIGN PATENT DOCUMENTS

| 0502769 | 9/1992 | European Pat. Off. . |
| 2191945 | 12/1987 | United Kingdom . |

OTHER PUBLICATIONS

Hawley's Condensed Chemical Dictionary, twelfth edition; Richard Lewis, ed. 1993.

*Primary Examiner*—Margaret W. Glass
*Attorney, Agent, or Firm*—Oblon, Spivak, McClelland, Maier & Neustadt, P.C.

[57] ABSTRACT

An emulsion of an oily phase in a surfactant-free gelled aqueous phase containing expanded hollow thermoplastic particles of acrylonitrile polymer or copolymer. The particles ensure the dispersion of the oily phase in the gelled aqueous phase and are preferably particles of expanded copolymers of acrylonitrile and acrylic or styrene-based monomers and/or vinylidene chloride. The emulsion obtained can be employed, for example, for the care or cleansing of skin and/or hair or for use in a skin make-up. It can also form a dermatological product.

25 Claims, No Drawings

SURFACTANT-FREE OIL-IN-WATER EMULSION STABILIZED BY HOLLOW THERMOPLASTIC PARTICLES

BACKGROUND OF THE INVENTION

1. Field of the Invention

The present invention relates to an oil-in-water (O/W) emulsion containing no surfactant. This emulsion is preferably in the form of a cream or a milk, which is white or colored and intended especially for the cosmetic treatment of the skin (body, face, etc.) and/or the hair. This cream may also be used as a make-up, a make-up remover or may serve as a dermatological treatment composition for the skin and/or the hair.

2. Discussion of the Background

For various reasons including their great comfort during use and their coolness, oil-in-water emulsions are widely employed today in the cosmetic and dermatological fields. These emulsions comprise an oily phase dispersed in an aqueous phase and one or more surfactants which stabilize the dispersion obtained. They have the disadvantage, however, of containing surfactants: it is well known that surfactants irritate the skin. Attempts are therefore increasingly being made to get rid of them.

Furthermore, the presence of surfactants in most cases requires the manufacture of the emulsion with heating, and this appreciably limits the nature of the active substances to be introduced into the emulsion. In particular, this process rules out the use of heat-sensitive active substances.

There is therefore a continuing need for an O/W emulsion which does not exhibit the disadvantages of those known so far and, in particular, one containing no surfactant.

DETAILED DESCRIPTION OF THE INVENTION

The present invention addresses these problems by providing a surfactant-free emulsion, preferably a cosmetic emulsion, of an oily phase in a gelled aqueous phase, characterized in that it contains expanded hollow thermoplastic particles of acrylonitrile polymer or copolymer ensuring the dispersion of the oily phase in the aqueous phase. In addition, the invention emulsion advantageously contains no monoalcohol and contains a cosmetically and/or pharmaceutically acceptable medium.

The invention emulsion has the advantage of not containing surfactant and therefore of not being irritating to the skin and also is very soft in application by virtue of the presence of the hollow particles. In addition, the use of hollow particles for stabilizing the invention emulsion enables it to be manufactured cold, which is easier and less costly than the conventional heating process carried out in most cases when surfactants are employed. Cold manufacture permits, for example, the introduction of heat-sensitive active substances without risk of deterioration of these active substances. Moreover, the use of hollow particles makes it possible to obtain a composition having a very pleasant texture which is not greasy despite the presence of oils, and which is not tacky despite the presence of gelling agents.

Another subject of the present invention is the use of the emulsion described above for the cosmetic treatment of the skin (for example nutrition, hydration, protection, cleaning, make-up, etc.) and/or of hair (protection, smoothing, etc.) and for the preparation of a cream intended for the treatment of diseases of the skin (for example mycoses, acne, inflammations, psoriasis, etc.) and/or of hair. A further subject of the present invention is a process for cosmetic treatment comprising applying the emulsion defined above to the skin and/or to hair. The term "skin" as used herein refers to all skin, including skin on the eye lids, etc.

A further subject of the present invention is the use of expanded hollow thermoplastic particles of acrylonitrile polymer or copolymer for dispersing, preferably without any surfactant, an oily phase in a gelled aqueous phase and for stabilizing the emulsion obtained.

It is known from the paper by C. Levine (Colloids and Surfaces, 1989, volume 38, pages 325 to 343, "Stabilization of Emulsions by Fine Particles. I. Partitioning of particles between continuous phase and oil/water interface") to employ fine silica particles rendered hydrophobic by surface treatment in order to stabilize dispersions containing no surfactant, but this document does not allow a person skilled in the cosmetic art to be led to the present invention, because, on the one hand, it relates to a quite different technical field (that of heavy oils and bitumens) and, on the other hand, because the teaching which is given therein does not lead to a homogeneous system but to coarse dispersions in which the droplets are visible to the naked eye. A cosmetic emulsion is a homogeneous dispersion of two phases, one in the other. The particles which are employed by Levine are different in their nature from those which make it possible to obtain the emulsion according to the present invention. For example, the present invention provides an emulsion which is as nonirritative as possible and which has good sensory properties, and which is very soft in application.

FR-A-2208642 describes a liquid cosmetic composition with two distinct phases, one consisting of water and of organic solvent (ethanol or propanol) and the other consisting of oil, finely divided particles being situated at the interface of the two phases. The particles consist of inorganic substances or of synthetic organic substances such as polyvinyl chloride. These particles are intended to facilitate the formation of oil droplets in the hydroalcoholic medium.

Because of the type of product obtained, namely a two-phase composition, and because of the presence of solvent consisting of a monoalcohol, this document does not lead a person skilled in the art to employ thermoplastic hollow particles to stabilize an oil-in-water emulsion containing no monoalcohol. In the present invention a homogeneous emulsion which is as nonirritating as possible is provided, preferably without monoalcohol, and not a two-phase composition containing alcohol or surfactants which may be irritants.

It is known according to EP-392426 to employ polymethyl methacrylate particles in order to introduce into a gelled system an active substance such as an oil, which is adsorbed onto the particles. However, particles of this type make it possible to introduce only a small quantity of oil into a gel, and not to obtain the dispersion of an oily phase in an aqueous phase, as will be shown by the comparative test described below.

In general, particles which may be used in the invention may be made of any expanded acrylonitrile polymer or copolymer which is nontoxic and nonirritating to the skin. The density of the particles is preferably chosen to be in the range extending from 15 kg/m$^3$ to 200 kg/m$^3$ and, better, from 40 kg/m$^3$ to 120 kg/m$^3$ and, still better, from 60 kg/m$^3$ to 80 kg/m$^3$ including all values and subranges between these several limits. To obtain this low density, particles of expanded polymers or copolymers which are preferably based on acrylonitrile and an acrylic or styrene-based monomers and/or vinylidene chloride are advantageously employed.

It is possible, for example, to employ a copolymer containing: from 0% to 60% of units derived from vinylidene chloride, from 20% to 90% of units derived from acrylonitrile and from 0% to 50% of units derived from an acrylic or styrene-based monomer, the sum of the percentages of the materials (by weight) being equal to 100. The acrylic monomer is, for example, a methyl or ethyl acrylate or methacrylate. The styrene-based monomer is, for example, α-methylstyrene or styrene.

The particles employed in the present invention are preferably hollow particles of an expanded copolymer of vinylidene chloride and acrylonitrile or a copolymer of vinylidene chloride, acrylonitrile and a methacrylate. These particles may be dry or hydrated and may be obtained, for example, according to the processes of the following patents and patent applications: EP-56219, EP-348372, EP-486080, EP320473, EP-112807 and U.S. Pat. No. 3,615,972 all incorporated herein by reference. The internal cavity of the particles contain, in principle, a gas which may be air, nitrogen or a hydrocarbon such as isobutane or isopentane.

The particles of the invention advantageously have a particle size ranging from 1 µm to 80 µm and, still better, ranging from 10 µm to 50 µm and, still better, from 10 µm to 30 µm including all values and subranges between these several limits.

Particles useful in the invention include, for example, microspheres of expanded terpolymer of vinylidene chloride, acrylonitrile and methacrylate, which are sold by the company Nobel Casco under the trademark EXPANCEL under references 551 DE 50 (particle size of approximately 40 µm), 551 DE 20 (particle size of approximately 30 µm and density of approximately 65 kg/m$^3$), 551 DE 12 (particle size of approximately 12 µm), 551 DE 80 (particle size of approximately 80 µm) and 461 DE 50 (particle size of approximately 50 µm). It is also possible to employ microspheres made of the same expanded terpolymer which have a particle size of approximately 18 µm and a density of approximately 70 kg/m$^3$, called EL 23 in the Examples below, or which have a particle size of approximately 34 µm and a density of approximately 20 kg/m$^3$, called EL 43 below.

In addition to their stabilization effect the particles of the invention impart lightness and mattness in application to the emulsions containing them.

In the emulsion compositions of the present invention from 0.1% to 10% by weight of particles are preferably employed, relative to the total weight of the composition and, better, from 0.5% to 5% by weight including all values and subranges between these several limits.

The emulsions according to the invention preferably comprise an aqueous phase gelled with the aid of at least one gelling agent, especially a hydrophilic gelling agent, with the result that the viscosity of the continuous aqueous phase is sufficiently high to permit good stability of the emulsion with time and to prevent the particles, whose density is extremely low, from rising to the surface and thus causing a destabilization of the emulsion.

The invention gelling agent(s) include carboxyvinyl (carbomer) polymers such as those sold by Goodrich under the names Carbopol, polyacrylates and polymethacrylates such as the products sold by Guardian under the names of Lubrajel or Norgel or by Hispano Chimica under the name Hispagel, polyacrylamides such as the product sold by Seppic under the name Sepigel 305, polysaccharides such as alginates, cellulose and its derivatives, especially carboxymethyl cellulose, hydroxymethyl cellulose, hydroxypropyl cellulose and microcrystalline cellulose, natural gums such as xanthan gum, guar gum, carob gum, acacia gum, scleroglucans, chitin and chitosan derivatives, carrageenans, or clays such as montmorillonite, bentones and aluminium and magnesium silicates (Veegum).

The quantity of gelling agent employed in the emulsion of the invention depends on the nature of the gelling agent(s) employed. It may, for example, range from 0.1% to 10% by weight and preferably from 0.2 to 6% by weight relative to the total weight of the emulsion including all values and subranges between these several limits.

The oily phase of the emulsion may be present in from 0.1 to 30% by weight and, better, from 5 to 15% by weight relative to the total weight of the emulsion, including all values and subranges between these several limits and may include oils, and optionally, other fatty substances.

Mineral oils, oils of animal origin, vegetable oils, synthetic oils, silicone oils and fluorinated oils are included among the oils useful in the invention. Among the mineral oils it is possible to mention, for example, liquid paraffin, vaseline oil and mineral oils which have a boiling point between 300° and 400° C. Perhydrosqualene may be mentioned, for example, among the oils of animal origin. Among the vegetable oils it is possible to mention, for example, sweet almond oil, calophyllum oil, palm oil, apricot kernel oil, avocado oil, jojoba oil, olive oil, castor oil, cereal germ oils (maize germ oil) and the liquid fraction of karite butter.

Among the synthetic oils there may be mentioned, for example, hydrogenated polyisobutene, fatty acid esters such as purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate and propylene glycol dicaprylate, esters derived from lanolic acid, such as diisopropyl lanolate and isocetyl lanolate, acetyl glycerides, alcohol and polyalcohol octanoates and decanoates such as those of glycol and of glycerol, and alcohol and polyalcohol ricinoleates.

Among silicone oils there may be mentioned, for example, cyclomethicones, polydimethylsiloxanes of low molecular weight (silicone oil) or of high molecular weight (silicone gum), polymethylsiloxanes, dimethiconols, phenylated polydimethylsiloxanes, siloxanols of low molecular weight and of high molecular weight and trimethylsiloxysilicates. Among fluorinated oils there may be mentioned, for example, perfluoroethers and fluorinated silicones.

Other fatty substances optionally to be present in the oily phase may be, for example, fatty acids, fatty alcohols and waxes.

In addition, the emulsions of the invention may contain adjuvants which are typical in the cosmetic or dermatological field, such as hydrophilic or lipophilic active agents, stabilizers, antioxidants, perfumes, fillers, sunscreens, colorants (pigments and dyes) and lipid vesicles. These adjuvants are employed in proportions which are typical in emulsions employed in the cosmetic or dermatological field, for example, from 0.01% to 20% by weight relative to the total weight of the emulsion and, depending on their nature, they are introduced into the gelled aqueous phase or into the oily phase of the emulsion.

Hydrophilic active substances useful herein include proteins or protein hydrolysates, amino acids (hydroxyproline, proline, etc.), polyols such as glycerine, sorbitol, butylene glycol, propylene glycol or polyethylene glycol, allantoin, guanosine, sugars and sugar derivatives, water-soluble vitamins such as ascorbic acid (vitamin C), hydroxyacids and their salts and water-soluble specific active agents such as hydrating, antiwrinkle, slimming, nutrient, softening and similar active agents.

Lipophilic active agents useful herein include, for example, liposoluble vitamins such as retinol (vitamin A) and its derivatives (retinyl palmitate), tocopherol (vitamin E) and its derivatives, sunscreens, ceramides and liposoluble specific active agents such as slimming active agents and agents active against free radicals.

It is obvious that the list of the hydrophilic or lipophilic active agents given above is not by any means exhaustive.

The emulsions forming one subject of the invention find their application in a large number of cosmetic and/or dermatological treatments of the skin and hair, including the scalp, especially for the care, cleansing and make-up of the skin, for hair care and for the therapeutic treatment of the skin, of hair and of the mucosa. These emulsions may, for example, be employed in products for facial care or make-up for dry skins or greasy skins.

Thus, for example, for the preparation of products for dry skin it is possible to introduce into the gelled aqueous phase hydrating water-soluble active substances such as, for example, glycerine, propylene glycol, sorbitol, proline, pyrrolidonecarboxylic acid and its derivatives, urea, hydrolysed collagen, Aloe Vera gel, hyaluronic acid and its derivatives, dimethylsilanol hyaluronate, allantoin, D-panthenol and sodium lactate.

On the other hand, treatment products for greasy skins may be obtained by introducing into the gelled aqueous phase water-soluble active substances such as provitamin B5, which is employed as emollient, or an antibacterial substance such as 3,4-transthiolanediol S-dioxide.

The emulsions according to the invention may also be employed as make-up removal or cleansing products for the face in the form of creams, milks or masks, for example, or as make-up products when incorporating fillers, pigments or dyes. It is possible, in particular, to obtain products for the complexion, cheek blushers, mascaras, foundations, tinted creams, colorant products for the body such as tinted products giving a natural suntan effect.

The emulsions of the invention may also be employed as antisun products by the introduction of water-soluble or liposoluble screens for protecting the skin and/or hair from UV radiation. As water-soluble sunscreens which may be introduced into the gelled aqueous phase it is possible to mention, for example, 2-hydroxy-4-methoxybenzophenone-5-sulphonic acid sold by BASF under the name Uvinul MS 40. As liposoluble sunscreens to be introduced into the oily phase it is possible to mention, for example, 2-ethylhexyl paramethoxycinnamate sold by Givaudan under the name Parsol MCX or 2-hydroxy-4-methoxybenzophenone sold by BASF under the name Uvinul M 40.

The emulsions according to the invention may also be employed in the preparation of products for use after exposure to the sun, containing, for example, vitamin F and the hydrating agents mentioned above as soothing active agents.

It is also possible to obtain slimming products by introducing water-soluble or liposoluble slimming active substances into the gelled aqueous phase or into the oily phase respectively. Among the water-soluble slimming active substances it is possible to mention xanthine derivatives such as caffeine, theobromine, theophylline, L-carnitine, dimethylaminoethyltheophylline hydrochloride, silicon derivatives of the methylsilanol theophyllinacetate alginate type, or plant derivatives such as hydroglycolic extracts of English ivy, of brown algae and of fresh wild pansy. Among the liposoluble slimming active substances there may be mentioned DL-alphatocopherol nicotinate, the oily extract of ginseng root (Panax ginseng), the oily extract of English ivy (Hedera helix), the oily extract of dried arnica flowers (Arnica montana L.), and the oily extract of algae (Fucus vesiculosus).

The emulsions of the invention may also be employed as products for heavy legs, containing, as water-soluble active substances, ginkgo biloba, melilot or ruscus and oils traditionally employed as emollients.

Finally, the emulsions according to the invention may also be employed in dermatology, for example, for the care of sensitive or irritated skins, for the treatment of psoriasis, of eczema, of acne or of mycoses, after introduction of appropriate active agents into the emulsion, such as antiinflammatory, antifungal, antiparasite and antipruritic agents, antiseborrhoeic agents, keratolytic agents or antiacne agents.

In general, the emulsions according to the invention can be prepared by cold (i.e., room temperature and below) processes known in the cosmetic and dermatological fields. It is possible, for example, first of all to prepare an aqueous gel by mixing the gelling agent and water and then to add thereto the active substances and other hydrophilic adjuvants and next to disperse therein the hollow particles. The fatty phase containing the oils and fatty substances, the active substances and other hydrophobic adjuvants, is then emulsified in this aqueous gel with stirring for a few minutes at ambient temperature. The gel preparation stage itself is liable to require slight heating, but any heat-sensitive active substances can always be added cold.

The product obtained is a cream-gel which exhibits excellent cosmetic properties, especially where the feel and the appearance are concerned, enabling it to be employed as a base for cosmetic products.

EXAMPLES

Particles of different nature in an oil-in-water emulsion were tested with a view to comparing their dispersing action. The composition in wt. % of the emulsion was the following:

| | |
|---|---|
| Cyclomethicone | 10.% |
| Carbomer (gelling agent) | 0.8% |
| Triethanolamine (neutralizing agent) | 0.8% |
| Particles | 1% |
| Water | q.s. 100% |

The results are given in the Table below. It was found that only the Expancel particles ensure a good dispersion of the oily phase in the aqueous phase.

| Filler type | Results |
|---|---|
| Polytrap 6603 (polymethyl methacrylate); aggregates from 200 μm to 1200 μm. Relative density: 0.06 | Coarse dispersion. Salting-out of oil at the surface on centrifuging |
| Expancel EI 23 | Ivory-coloured gleaming cream. Good stability on centrifuging |

The following examples illustrate the present invention but are not limiting thereof. In these examples the percentages are given by weight.

Example 1: Eyeline care

| Phase A1 | | |
|---|---|---|
| Guanosine | | 0.01% |
| Hydroxyproline | | 1.00% |
| Stabilizers | | 0.30% |
| Demineralized water | q.s. | 100.% |
| Phase A2 | | |
| Demineralized water | | 22.00% |
| Glycerine | | 10.00% |
| Carbomer (gelling agent) | | 0.80% |
| Phase A3 | | |
| Triethanolamine (neutralizing agent) | | 0.80% |
| Phase B | | |
| Microspheres EL 23 | | 1.30% |
| Phase C | | |
| Maize germ oil | | 10.00% |
| Retinyl palmitate | | 0.15% |
| Perfume | | 0.30% |

Phase A1 was prepared by dissolving guanosine in water and then adding the hydroxyproline and the stabilizers to it at ambient temperature.

Phase A2 was prepared separately by swelling the carbomer, with turbine stirring, at ambient temperature in water to which glycerine had been added. Phase A3 was then introduced into phase A2.

Phase C was prepared by mixing the constituents at ambient temperature.

Phase A1 and the mixture of phases A2 and A3 were homogenized. Phase B was next dispersed therein with stirring and then phase C was added.

After turbine stirring for 15 min a cream-gel intended for eyeline care is obtained. The product obtained was very soft in application and its formulation remains wholly stable over the course of time.

Example 2: Aftershave fluid

| Phase A1 | | |
|---|---|---|
| Guanosine | | 0.01% |
| Allantoin | | 0.20% |
| Stabilizers | | 0.30% |
| Demineralized water | q.s. | 100.% |
| Phase A2 | | |
| Demineralized water | | 22.00% |
| Glycerine | | 7.00% |
| Carbomer (gelling agent) | | 0.40% |
| Xanthan gum (gelling agent) | | 0.10% |
| Phase A3 | | |
| Triethanolamine (neutralizing agent) | | 0.40% |
| Phase B | | |
| Microspheres EL 23 | | 0.80% |
| Phase C | | |
| Cyclomethicone | | 8.00% |
| Perfume | | 0.50% |

The procedure was the same as in Example 1. An aftershave fluid was obtained which is smooth and nonirritating and which has a very soft feel.

Example 3: Hydrating body balm

| Phase A1 | | |
|---|---|---|
| D-Panthenol | | 1.0% |
| Urea | | 2.0 |
| Sodium lactate | | 1.0 |
| Stabilizers | | 0.4 |
| Demineralized water | q.s. | 100% |
| Phase A2 | | |
| Demineralized water | | 25.0% |
| Glycerine | | 5.0% |
| Carbomer (gelling agent) | | 0.8% |
| Xanthan gum (gelling agent) | | 0.1% |
| Phase A3 | | |
| Triethanolamine (neutralizing agent) | | 0.8% |
| Phase B | | |
| Microspheres EL 23 | | 1.0% |
| Phase C | | |
| Liquid fraction of karite butter | | 8.0% |
| Perfume | | 0.3% |

The procedure was the same as in Example 1. A very soft body balm was obtained, the application of which was very pleasant and which hydrates the skin well without causing irritation.

| Phase A | | |
|---|---|---|
| Acacia gum (gelling agent) | | 0.62% |
| Carragheenan (gelling agent) | | 1.50% |
| Xanthan gum (gelling agent) | | 0.25% |
| Montmorillonite (gelling agent) | | 2.00% |
| Butylene glycol | | 3.00% |
| Stabilizer | | q.s. |
| Demineralized water | q.s. | 100 |
| Phase B | | |
| Wheat starch (filler) | | 2.00% |
| Titanium dioxide (pigment) | | 2.00% |
| Yellow iron oxide (pigment) | | 0.03% |
| Expancel 551 DE 20 | | 6.00% |
| Phase C | | |
| Liquid paraffin | | 5.00% |

The procedure consisted in preparing phase A by dispersing all the constituents in water at ambient temperature and then forming a paste of phase B in phase A and next incorporating the fatty phase by stirring vigorously for 10 min.

The mask obtained has a very light texture. It is very soft when applied and does not dry the skin.

Example 5: Cheek blusher

| Phase A | | |
|---|---|---|
| Carbomer (gelling agent) | | 0.60% |
| Triethanolamine (neutralizing agent) | | 0.60 |
| Stabilizers | | q.s. |
| Glycerine | | 2.00 |
| Quinoline yellow (dye) | | 0.07 |
| Ponceau disodium salt (dye) | | 0.09% |
| Alizarin Green disodium salt (dye) | | 0.04% |
| Demineralized water | q.s. | 100% |
| Phase B | | |
| Cyclomethicone/dimethiconol (mixture sold by Dow Corning under | | 4.00% |

-continued

| | |
|---|---|
| the name DC 1401 Substantivity Aid Fluid | |
| Hydrogenated polyisobutene | 4.00% |
| Phase C | |
| Expancel 551 DE 20 | 0.80% |

The procedure consisted of preparing the gelled aqueous phase A at 80° C. by mixing the various constituents in water and then leaving it to cool to ambient temperature while stirring. Phase C is next added to it with fairly slow stirring and phase B is incorporated therein with moderate stirring for about ten minutes.

A very soft gelled cheek blusher was obtained which is easy to spread and which finally gives a very natural powdered effect.

Example 6: Tinted gel

| | |
|---|---|
| Phase A | |
| Carbomer (gelling agent) | 1.50% |
| Triethanolamine (neutralizing agent) | 1.50% |
| Polyethylene glycol | 8.40% |
| Stabilizers | 0.30% |
| Glycerine | 2.00% |
| Quinoline Yellow (dye) | 0.07% |
| Ponceau disodium salt (dye) | 0.09% |
| Alizarin Green disodium salt (dye) | 0.04% |
| Demineralized water | q.s. 100.% |
| Phase B | |
| Cyclomethicone/dimethiconol (mixture sold by Dow Corning under the name DC 1401 Substantivity Aid Fluid) | 5.00% |
| Phase C | |
| Microspheres EL 23 | 1.00% |

The procedure was the same as in the preceding example.

A tinted gel for the face or for the body was obtained, which is very soft when applied, easy to spread and to distribute uniformly. This gel is not greasy and is not tacky.

Example 7: Dermatological cream

| | |
|---|---|
| Phase A | |
| Carbomer (gelling agent) | 6.00% |
| Sodium hydroxide (neutralizing agent) | 1.00% |
| Demineralized water | q.s. 100% |
| Phase B | |
| Microspheres EL23 | 1.00% |
| Phase C | |
| Fluid vaseline oil | 6.00% |
| Phase D | |
| Clobetasol 17 propionate (anti-inflammatory) | 0.01% |
| Propylene glycol | 5.00% |

The procedure consisted of preparing phase A, in introducing phase B into it with moderate stirring and in then incorporating phase C dropwise while maintaining the stirring, in homogenizing with magnetic stirring and, finally, in adding phase D to it with stirring.

A cream which is very soft when applied and suitable for the treatment of psoriasis was obtained.

This application is based on French patent application 94-08561, incorporated herein by reference.

What is claimed as new and is desired to be secured by Letters Patent of the United States is:

1. A surfactant-free emulsion of an oily phase in a gelled aqueous phase, comprising oil, water, at least one gelling agent and expanded hollow thermoplastic particles of an acrylonitrile polymer or an acrylonitrile copolymer.

2. The emulsion according to claim 1, characterized in that it is free of monoalcohol.

3. The emulsion according to claim 1, wherein the at least one gelling agent is selected from the group consisting of carboxyvinyl polymers, polyacrylamides, polyacrylates, polymethacrylates, polysaccharides, natural gums and clays.

4. The emulsion according to claim 1, wherein the particles have a particle size of 1 to 80 μm.

5. The emulsion according to claim 1, wherein the particles have a particle size of 10 to 50 μm.

6. The emulsion according to claim 1, wherein the particles have a density of 15 to 200 kg/m$^3$.

7. The emulsion according to claim 1, wherein the particles have a density of 40 to 120 kg/m$^3$.

8. The emulsion according to claim 1, wherein the particles are present in from 0.1% to 10% by weight relative to the total weight of the emulsion.

9. The emulsion according to claim 1, wherein the at least one gelling agent is present in from 0.1 to 10% by weight relative to the total weight of the emulsion.

10. The emulsion according to claim 1, wherein the oily phase represents from 0.1% to 30% by weight relative to the total weight of the emulsion.

11. The emulsion according to claim 1, further comprising at least one additive selected from the group consisting of hydrophilic active substances, lipophilic active substances, stabilizers, antioxidants, perfumes, fillers, sunscreens, colorants and lipid vesicles.

12. A process for the cosmetic, dermatological or pharmaceutical treatment of skin and hair or both, comprising applying to the skin, the hair the emulsion according to claim 1.

13. A method for dispersing, without the use of a surfactant, an oily phase in a gelled aqueous phase, comprising the step of mixing expanded hollow thermoplatic particles of acrylonitrile polymer or copolymer with the aqueous gelled phase and the oily phase.

14. The method according to claim 13, wherein the particles have a particle size of 1 to 80 μm.

15. The method according to claim 13, wherein the particles have a particle size of 10 to 50 μm.

16. The method according to claim 13, wherein the particles have a density of 15 to 200 kg/m$^3$.

17. The method according to claim 13, wherein the particles have a density of 40 to 120 kg/m$^3$.

18. The method for dispersing, without the use of surfactant, an oily phase in a gelled aqueous phase, as claimed in claim 13, comprising the steps of adding expanded hollow thermoplastic particles of acrylonitrile polymer or copolymer to the aqueous gelled phase, followed by addition of the oily phase to the particle/gelled phase mixture.

19. The emulsion as claimed in claim 1, further comprising a cosmetic or dermatological adjuvant.

20. The emulsion according to claim 1, wherein the particles are expanded hollow particles of a copolymer containing from 0–60 wt. % vinylidene chloride units, from 20–90 wt. % acrylonitrile units and from 0–50 wt. % of (meth)acrylic or styrene units.

21. The emulsion according to claim 1, wherein the emulsion contains from 0.1% to 10% by weight of said expanded hollow thermoplastic particles.

22. The emulsion according to claim 21, wherein the amount of said particles ranges from 0.5 to 5% by weight.

23. The method according to claim 13, wherein the particles are expanded hollow particles of a copolymer containing from 0–60 wt. % vinylidene chloride units, from 20–90 wt. % acrylonitrile units and from 0–50 wt. % of (meth)acrylic or styrene units.

24. The method according to claim 13, wherein the emulsion contains from 0.1% to 10% by weight of said expanded hollow thermoplastic particles.

25. The method according to claim 24, wherein the amount of said particles ranges from 0.5 to 5% by weight.

* * * * *

UNITED STATES PATENT AND TRADEMARK OFFICE
CERTIFICATE OF CORRECTION

PATENT NO. : 5,637,291
DATED: : JUNE 10, 1997
INVENTOR(S) : ISABELLE BARA ET AL

It is certified that error appears in the above-identified patent and that said Letters patent is hereby corrected as shown below:

Column 4, line 43, "poiymethylsiloxanes" should read --polymethylsiloxanes--.

Column 10, line 41, "thermoplatic" should read --thermoplastic--.

Signed and Sealed this

Twenty-third Day of June, 1998

Attest:

BRUCE LEHMAN

*Attesting Officer*  *Commissioner of Patents and Trademarks*